(12) United States Patent
Zhang et al.

(10) Patent No.: US 11,768,149 B2
(45) Date of Patent: Sep. 26, 2023

(54) DEVICE FOR MEASURING FRICTIONAL FORCE AND FILM THICKNESS OF LUBRICATING OIL FILM IN DIFFERENT SURFACE VELOCITY DIRECTIONS

(71) Applicant: QINGDAO UNIVERSITY OF TECHNOLOGY, Shandong (CN)

(72) Inventors: Jianjun Zhang, Qingdao (CN); Hewei Lu, Qingdao (CN); Qinglun Che, Qingdao (CN); Jiahao Zhang, Qingdao (CN); Zhaogang Jing, Qingdao (CN); Chenglong Liu, Qingdao (CN); Feng Guo, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 217 days.

(21) Appl. No.: 17/402,243

(22) Filed: Aug. 13, 2021

(65) Prior Publication Data
US 2022/0050045 A1    Feb. 17, 2022

(30) Foreign Application Priority Data

Aug. 13, 2020    (CN) .......................... 2020108140072

(51) Int. Cl.
*G01N 19/02*    (2006.01)
*G01N 33/30*    (2006.01)
*G01B 5/06*    (2006.01)

(52) U.S. Cl.
CPC ............. *G01N 19/02* (2013.01); *G01B 5/066* (2013.01); *G01N 33/30* (2013.01)

(58) Field of Classification Search
CPC ..... G01N 19/02; G01N 33/30; G01N 33/2888
(Continued)

(56) References Cited

U.S. PATENT DOCUMENTS 1,989,627 A * 1/1935 Sage ............................. 340/631
1,990,771 A * 2/1935 Boden ..................... G01N 33/30
73/9
(Continued)

FOREIGN PATENT DOCUMENTS

CN    107228629 A  * 10/2017
CN    107271645 A  * 10/2017
(Continued)

OTHER PUBLICATIONS

ESPACENET Machine Translation of CN 107228629 A Which Originally Published On Oct. 3, 2017. (Year: 2017).*
(Continued)

*Primary Examiner* — David A. Rogers
(74) *Attorney, Agent, or Firm* — Oliff PLC

(57) ABSTRACT

A device measures a frictional force and a film thickness of a lubricating oil film in different surface velocity directions. The device includes an experiment bench. A translation stage is mounted to the experiment bench, and is linearly movable. A main shaft system is mounted to the experiment bench. A glass disc is mounted to the main shaft system and is rotatable. An arcuate guide rail is disposed on the translation stage. A rotary base is mounted to the arcuate guide rail and is movable along the arcuate guide rail. A loading system is mounted to the rotary base. A steel ball of the loading system and the glass disc are movable relative to each other. A rotary bearing in the rotary base is configured to convert a frictional force generated from the relative movement to a pressure allowed to be collected by a pressure sensor on the rotary base.

10 Claims, 11 Drawing Sheets

(58) Field of Classification Search
USPC .......................................................... 73/9, 10
See application file for complete search history.

(56) References Cited

U.S. PATENT DOCUMENTS

| | | | | |
|---|---|---|---|---|
| 3,952,566 | A * | 4/1976 | Jacobson | F16C 19/52 |
| | | | | 73/593 |
| 5,311,763 | A * | 5/1994 | Gibbs, Jr. | G01M 13/04 |
| | | | | 73/9 |
| 5,377,525 | A * | 1/1995 | Hutchinson | G01N 19/02 |
| | | | | 73/9 |
| 5,388,442 | A * | 2/1995 | Kumar | G01N 33/30 |
| | | | | 73/54.28 |
| 5,795,990 | A * | 8/1998 | Gitis | G01N 19/02 |
| | | | | 73/9 |
| 5,861,954 | A * | 1/1999 | Israelachvili | G01N 19/02 |
| | | | | 73/862.632 |
| 6,167,745 | B1 * | 1/2001 | Hamer | G01N 19/02 |
| | | | | 73/9 |
| 6,691,551 | B2 * | 2/2004 | Otaki | G01N 33/30 |
| | | | | 73/9 |
| 7,373,800 | B2 * | 5/2008 | Domeier | G01N 11/10 |
| | | | | 73/9 |
| 7,784,326 | B2 * | 8/2010 | Domeier | G01N 3/56 |
| | | | | 73/9 |
| 7,886,571 | B2 * | 2/2011 | Lee | G01N 3/42 |
| | | | | 73/1.01 |
| 8,051,699 | B2 * | 11/2011 | Linares | G01N 3/56 |
| | | | | 73/7 |
| 9,702,809 | B2 * | 7/2017 | Wolf | G01N 11/00 |
| 10,161,840 | B2 * | 12/2018 | Padgurskas | G01N 3/56 |
| 10,281,388 | B2 * | 5/2019 | Dube | G01N 3/56 |
| 10,429,284 | B1 * | 10/2019 | Nation | G01N 3/56 |
| 10,788,476 | B2 * | 9/2020 | Hamer | G01N 11/16 |
| 11,313,777 | B2 * | 4/2022 | Ramirez Gonzalez | |
| | | | | F16C 17/246 |
| 11,327,005 | B2 * | 5/2022 | Potier | G01N 3/56 |
| 2003/0054740 | A1 * | 3/2003 | Mansky | G01N 3/02 |
| | | | | 451/57 |
| 2004/0187556 | A1 * | 9/2004 | Abe | G01N 19/02 |
| | | | | 73/9 |
| 2013/0205880 | A1 * | 8/2013 | De Kraker | G01N 33/2888 |
| | | | | 73/114.55 |

FOREIGN PATENT DOCUMENTS

| | | | | |
|---|---|---|---|---|
| CN | 108169120 | A | * | 6/2018 |
| CN | 109060648 | A | * | 12/2018 |
| CN | 105628534 | B | * | 1/2019 |
| CN | 109520921 | A | * | 3/2019 |
| CN | 114112896 | A | * | 3/2022 |
| FR | 3094486 | A1 | * | 10/2020 |

OTHER PUBLICATIONS

ESPACENET Machine Translation of CN 107271645 A Which Originally Published On Oct. 20, 2017. (Year: 2017).*

* cited by examiner

DEVICE FOR MEASURING FRICTIONAL FORCE AND FILM THICKNESS OF LUBRICATING OIL FILM IN DIFFERENT SURFACE VELOCITY DIRECTIONS

TECHNICAL FIELD

The present invention discloses a device for measuring a frictional force and a film thickness of a lubricating oil film in different surface velocity directions.

BACKGROUND

Currently, an elastic fluid lubricant experiment bench measures a thickness and a frictional force of an oil film with the same velocity direction or a reverse velocity direction of a contact point between a ball and a disc. Point contact and line contact are ways of contact between most ball bearings and some bevel gears. During actual operation, a motion direction of a contact surface is relatively complex. For example, in a hypoid gear or a helical gear in a transmission system, a certain angle exists between surface velocity directions of two contact solids of a meshing contact pair. The contact motion directions are described as different surface velocity directions. In such a more general case in which two solids have different contact surface velocity directions, a frictional force between components and a shape and a thickness of a lubricating oil film vary accordingly. The existing experimental research on elastic fluid lubricant film measurement still lacks a feasible experimental measurement solution for a film thickness and a frictional force.

SUMMARY

In order to realize measurement of a frictional force of an elastic fluid contact pair and imaging of an oil film in different surface velocity directions, the present invention provides an external frictional force measurement device that guarantees imaging quality of an original oil film imaging system, so that point contact lubrication and friction conditions at different surface velocity conditions can be measured, and an angle between velocities of two contact solids can also continuously vary.

To Achieve the Above Objective, the Following Technical Solutions are Used in the Present Invention According to a first aspect, the present invention discloses a device for measuring a frictional force and a film thickness of a lubricating oil film in different surface velocity directions. The device includes an experiment bench. A translation stage is mounted to a top of the experiment bench. The translation stage is linearly movable under driving of a driving device. A main shaft system is mounted to the experiment bench. A glass disc is mounted to the main shaft system. The main shaft system is configured to be driven by a second driving device to rotate, so as to rotate glass disc. An arcuate guide rail is disposed on the translation stage. A rotary base is mounted to the arcuate guide rail and is movable along the arcuate guide rail. A loading system is mounted to the rotary base. A steel ball of the loading system and the glass disc are movable relative to each other. A rotary bearing adjacent to the loading base is configured to convert a frictional force generated from the relative movement to a pressure allowed to be collected by a pressure sensor on the rotary base.

In a further technical solution, the rotary base includes a turnable positioning stage, a loading base, a turnable shaft, and a bidirectional translation stage. The turnable positioning stage is mounted to the arcuate guide rail by using rollers. A top is connected to the loading base by using the turnable shaft. The bidirectional translation stage is mounted to one side of the turnable positioning stage. The bidirectional translation stage is connected to the loading base by using a rod. Two pressure sensors are mounted to two sides of the rod.

The bidirectional translation stage includes a body. Two sliders are mounted in the body. A first pressure sensor is mounted to one of the sliders, and a second pressure sensor is mounted to the other of the sliders. A bottom of each slider is threadedly mated with a threaded rod that is manually adjustable. By rotating the two threaded rods, face-to-face or opposite movement of the two pressure sensors can be realized.

In a further technical solution, the loading system includes a loading support, a loading lever, fulcrum bearings, a weight fixing rod, a weight tray, a weight support base, a loading adjustment rod, an adjustment guide block, a spring, a servo motor, a rigid coupler, and a steel ball. The loading support is mounted to the rotary base. The two fulcrum bearings are respectively mounted in circular holes in the middle of the loading support. The loading lever extends through the fulcrum bearings to be mounted in the middle of the loading support. One end of the loading lever is connected to the servo motor. The servo motor is connected to the steel ball by using the rigid coupler. A loading weight and the loading adjustment rod are mounted to an other end of the loading lever.

Further, the loading adjustment rod is threadedly connected to a rear end of the loading lever, the adjustment guide block and the spring are mounted to a lower end of the loading adjustment rod in sequence, and a lower end of the spring is connected to the loading support by using a connector.

Further, the weight support base is mounted to a rear end of the loading lever, the weight fixing rod is mounted to the weight support base, and the weight tray is mounted to the weight fixing rod.

Further, one end of the rigid coupler is connected to the steel ball by using threads of a rod, and an other end is connected to an output rod of the servo motor by using threads, so as to couple the motor to the steel ball for power transfer, and a main body of the servo motor is connected to a front end of the loading lever by using threads.

In a further technical solution, the device further includes an image capture system. The image capture system includes a displacement stage, a microscope support, a lens barrel bracket, a hand wheel, a focus wheel, a CCD, and a microscope. The displacement stage is mounted to a top of the microscope support. A support rod is mounted to the displacement stage. A support rod bracket of the microscope support is sleeved on the support rod and connected to the lens barrel bracket. The hand wheel and the focus wheel are mounted to the support rod bracket of the microscope support, to adjust a focus and a lens of the microscope and adjust a definition of interference fringes in an oil film image. Locking screws are screwed into a front of the lens barrel bracket to fix a main body of the microscope, so as to ensure that the image does not move during observation. The CCD and the microscope are mounted in the lens barrel bracket to realize image observation and data transmission.

The device for measuring a frictional force and a film thickness of a lubricating oil film in different surface velocity directions disclosed in the present invention has the following working principles.

The image capture system tunes an adjustment nut of the displacement stage to move a lens of the microscope in an x direction and a y direction, tunes the lens barrel bracket by using the hand wheel and the focus wheel to move the lens up and down in a z direction, so as to position an oil film image and adjust a focus to obtain a clear oil film interference fringe image, and adjusts the locking screws to fix the CCD and the lens of the microscope to observe the image.

Upon receipt of a force from the steel ball, the loading base transfers a frictional force to the rod by using the rotary bearing, so that the rod squeezes the pressure sensor, thereby indirectly measuring of a frictional force between a ball and a disc. During the experiment, the steel ball is in load contact with the glass disc under the circular disc, rotation of the glass disc and the steel ball in opposite directions causes relative movement between the glass disc and the steel ball, and a frictional force generated from the movement causes the loading base to tend to rotate relative to the rotary bearing. The frictional force is transferred through the rotary bearing to the rod connected to the loading base that is on one side of a motor base, and the rod is moved to a certain extent under the force to squeeze the sensor. Therefore, one of the two sensors oppositely mounted under the loading system receive a force. By converting a measured force arm, a component of the frictional force between the steel ball and the glass disc that is perpendicular to an axial direction of a rod of the steel ball can be obtained, thereby realizing conversion of the frictional force received by the steel ball to a pressure received by the pressure sensor. By means of correction by using other equations, an actual frictional force can be obtained.

The arcuate guide rail is laid on one side of the translation stage in a semicircular shape, and a center of circle of the guide rail is on a central axis of the translation stage, so as to ensure that a contact point of the ball remains unchanged when an angle of the rotary portion is changed. The guide rail is fastened on the translation stage by using countersunk screws located above, and the guide rail corresponds to an angle scale engraved on the translation stage, so that an oil film interference image at a specific angle can be obtained. Four circular truncated cone rollers are mounted under the turnable positioning stage, grooves of the rollers are precisely mated with an upper edge of the guide rail, the rollers are slidable along the guide rail, and the four rollers are evenly distributed on left and right sides of the guide rail to form a V-shaped constraint fitting the arcuate guide rail. In this way, it can be ensured that an upper surface of a support base and the translation stage always remain parallel to bear loads and overturning moments in all directions, and movement precision during sliding along the guide rail can be ensured. During the experiment, when a stroke angle scale is observed to reach a predetermined angle, an adjustment handle is rotated so that the fastening block moves inward perpendicularly to the arcuate guide rail, thereby increasing a positive pressure between the fastening block and the arcuate guide rail. In this way, a theoretical maximum frictional force between the fastening block and the arcuate guide rail also increases, so that the turnable positioning stage is stationary relative to the arcuate guide rail, avoiding an angle deflection between the ball and the disc during movement, thereby remaining the contact point between the ball and the disc unchanged during the experiment.

The adjustment guide block is connected to the spring, and the loading adjustment rod is connected to the guide block. The loading supports on both sides of the loading adjustment rod have vertical grooves thereon, so that a pressure on the spring below the loading adjustment rod is also vertical during up and down rotation of the loading adjustment rod, thereby realizing vertical loading and unloading of the spring, and ensuring stability during a step of adjusting the loading adjustment rod. In addition, the spring can buffer the loading of the steel ball, preventing the steel ball from impacting the glass disc when a pressure is applied to the lever and causing damage to a surface of the glass disc or a coating film below the glass disc, and ensuring stability of the loading.

By means of screw transmission of a screw and a slider, a translation stage driver can convert a rotary motion to a linear motion. In addition, since the device has characteristics such as reverse transmission self-locking and high transmission precision, relative positions of the parts may be conveniently adjusted and fixed, which is applicable to the movable translation stage which needs to be moved back and forth and locked in position. One end of the mechanism is mounted to an upper table, and an other end is fixed to a worktable. A double-row thrust ball bearing is mounted in the end mounted to the upper bench face to bear an axial force during the movement. A linear guide rail is fixed to the experiment bench by using screws, each guide rail slider is fixedly connected to a lower surface of the translation stage, and the hand wheel may be manually rotated to realize the back and forth movement of the translation stage, so as to use different guide rails of the glass disc and adjust a radius of rotation between the ball and the disc.

Beneficial Effects of the Present Invention are as Follows

The present invention is composed of eight parts: an experiment bench, a main shaft driving system, a translation stage driver, a translation stage, an image capture system, a main shaft system, a rotary base, and a loading system, which are precisely mated, exhibiting a scientific and practical design. Compared with an existing experiment bench device, on the basis of observation of a shape and a thickness of an oil film in different velocity directions, a rotary bearing is added. By means of a force transfer and conversion function of the rotary bearing, the frictional force between the ball and the disc that is not easy to directly observe to a positive pressure between the rod and the sensor, and then an actual resultant frictional force is calculated by analyzing the frictional force between the ball and the disc and based on a geometric relationship between a velocity of the ball a velocity of the disc, realizing the measurement of the frictional force of the point contact between the ball and the disc under entrainment of elastic fluid lubricant in different directions. The integrated combination of oil film measurement and frictional force measurement in different surface velocity directions helps analyze film formation of the oil film and friction and wear on a surface of a workpiece.

Figure 1:
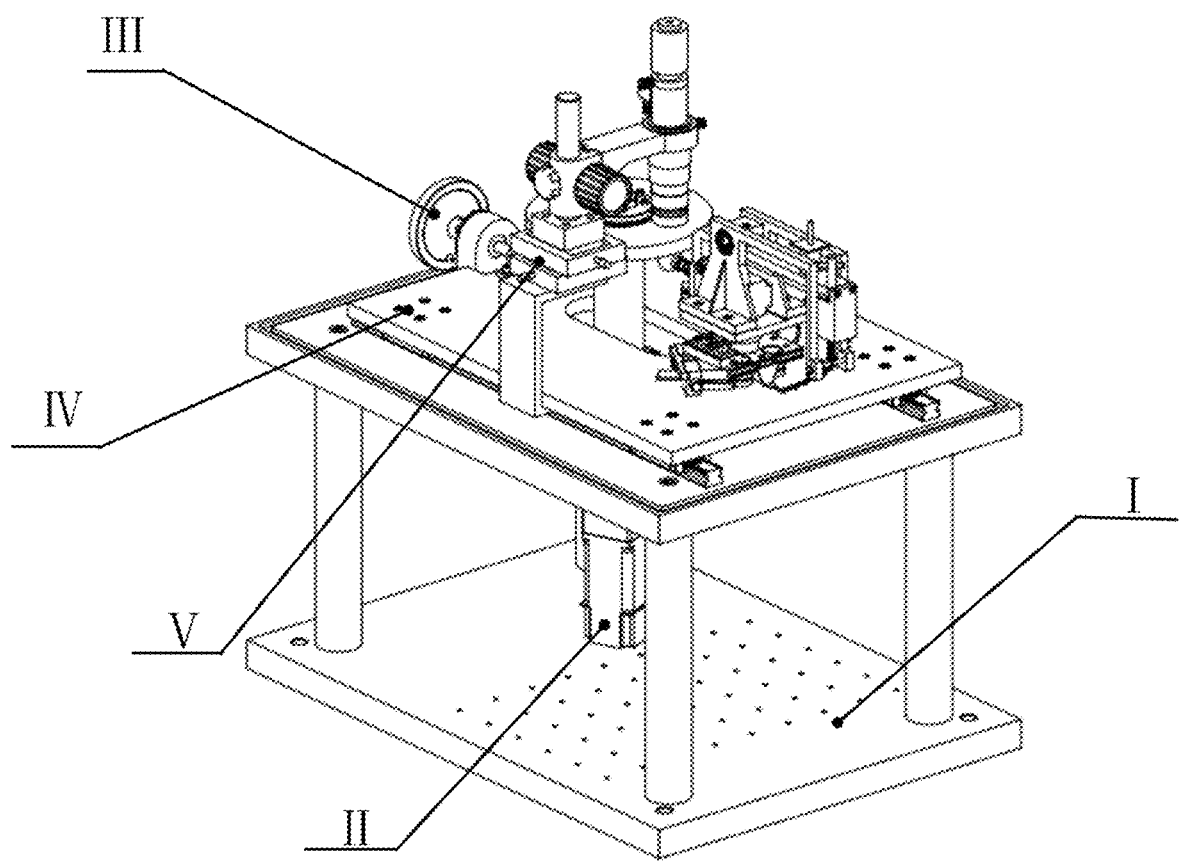
FIG. 1 and FIG. 2 are schematic structural diagrams of the present invention.

Experiment bench I, Main shaft driving system II, Translation stage driver III, Translation stage IV, Image capture system V, Main shaft system VI, Rotary base VII, Loading system VIII, Support post I-1, Lower base plate I-2, Support screw I-3, Upper table I-4, Linear guide rail I-5, Motor support post II-1, Motor vibration isolation pad II-2, Precise decelerator II-3, Threaded coupler II-4, Motor II-5, Driving rear seat III-1, Translation driving rod III-2, Rear seat end cover III-3, Hand wheel III-4, Retainer ring III-5, Worktable IV-1, Threaded pitch adjusting seat IV-2, Guide rail slider IV-3, Arcuate guide rail IV-4, First displacement stage V-1, Second displacement stage V-2, Connecting plate V-3, Support rod V-4, Microscope support V-5, Support rod bracket of microscope support V-6, Lens barrel bracket V-7, Hand wheel V-8, Focus wheel V-9, Locking screw V-10, CCD and microscope V-11, Main shaft VI-1, Glass disc VI-2, Steel pad VI-3, Glass disc pressing sleeve VI-4, Shaft inner sleeve VI-5, Outer sleeve VI-6, Upper end cover VI-7, Pre-tightening nut VI-8, Lower end cover VI-9, Second rubber pad VI-10, First bearing VI-11, Second bearing VI-12, First rubber pad VI-13, Turnable positioning stage VII-1, Bidirectional translation stage VII-2, First pressure sensor VII-3, Second pressure sensor VII-4, Turnable pillar VII-5, Loading base VII-6, Bearing seat VII-7, Adjustment handle VII-8, Fastening block VII-9, Rod VII-10, Rotary bearing VII-11, First loading support VIII-1, Second loading support VIII-2, Loading lever VIII-3, Fulcrum bearing VIII-4, Weight fixing rod VIII-5, Weight tray VIII-6, Weight support base VIII-7, Loading adjustment rod VIII-8, Adjustment guide block VIII-9, Spring VIII-10, Servo motor VIII-11, Rigid coupler VIII-12, Steel ball VIII-13.

DETAILED DESCRIPTION

It should be pointed out that the following detailed descriptions are all illustrative and are intended to provide further a description of the present invention. Unless otherwise specified, all technical and scientific terms used herein have the same meanings as those usually understood by a person of ordinary skill in the art to which the present invention belongs.

It should be noted that the terms used herein are merely used for describing specific implementations, and are not intended to limit exemplary implementations of the present invention. As used herein, the singular form is also intended to include the plural form unless the present invention clearly dictates otherwise. In addition, it should be further understood that, terms "comprise" and/or "include" used in this specification indicate that there are features, steps, operations, devices, components, and/or combinations thereof.

For convenience of description, the terms "upper", "lower", "left" and "right", if exist in the present invention, only indicate upper, lower, left and right directions consistent with those of the accompanying drawings, are not intended to limit the structure, and are used only for ease of description of the present invention and brevity of description, rather than indicating or implying that the mentioned device or element needs to have a particular orientation or needs to be constructed and operated in a particular orientation. Therefore, such terms should not be construed as a limitation on the present invention.

As described in the background, most lubricating oil film measurement devices in the known field can measure only an oil film under the same surface velocity direction of a ball and a disc, and an existing lubricating oil film measurement device applicable to different surface velocity directions does not combine measurement of a frictional force. The present invention aims to provide a device capable of measuring a lubricating oil film and a frictional force in different surface velocity directions, so as to conduct a more in-depth study on a thickness and a shape of an actual oil film and friction and wear of components.

Figure 2:
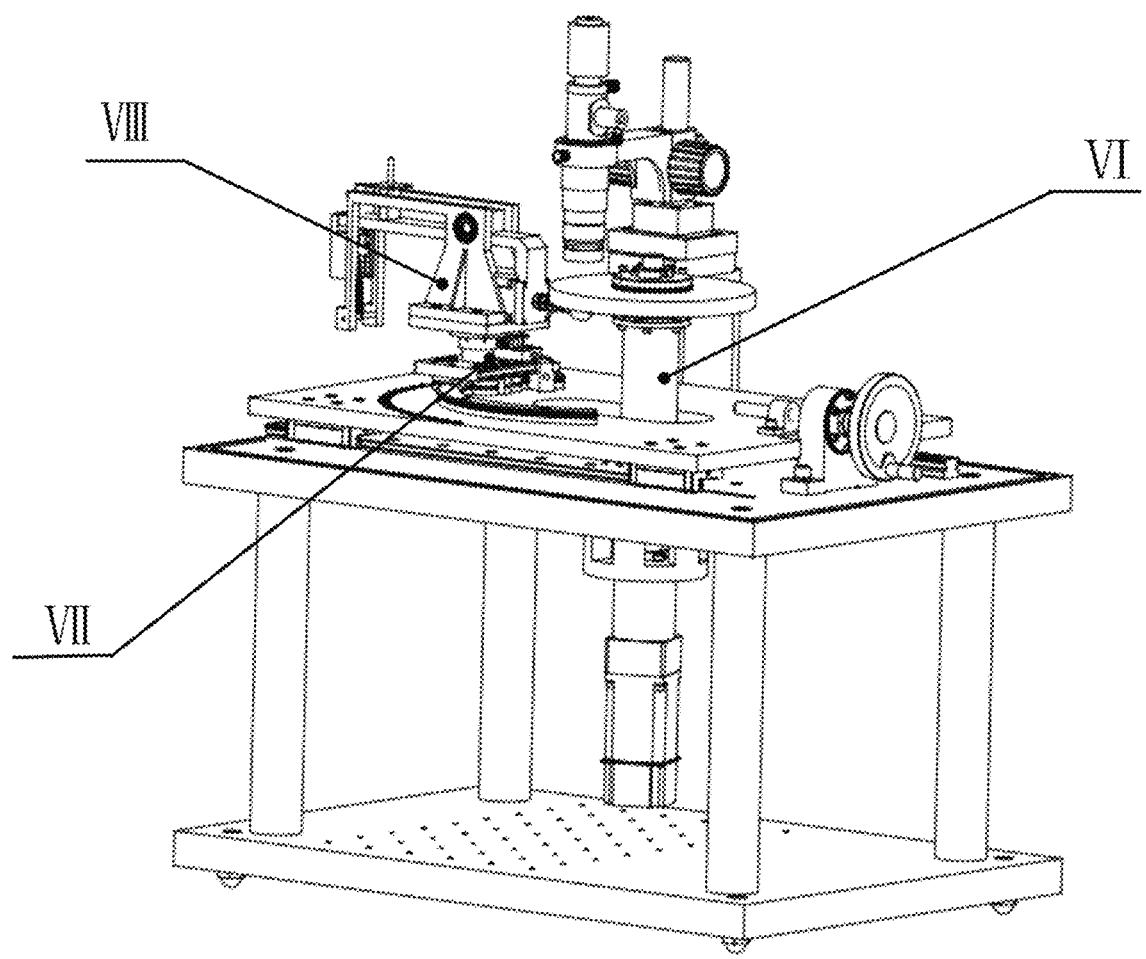

A typical implementation provided in the present invention is shown in FIG. 1 and FIG. 2. A device for measuring a frictional force and a film thickness of a lubricating oil film in different surface velocity directions mainly includes eight parts: an experiment bench I, a main shaft driving system II, a translation stage driver III, a translation stage IV, an image capture system V, a main shaft system VI, a rotary base VII, and a loading system VIII.

The translation stage IV is disposed on a top of the experiment bench I. The translation stage IV is linearly movable under driving of the translation stage IV. The main shaft system VI is mounted to the experiment bench I. A glass disc is mounted to the main shaft system VI. The main shaft system VI is configured to be driven by the main shaft driving system II to rotate, so as to rotate glass disc. An arcuate guide rail is disposed on the translation stage IV. The rotary base is mounted to the arcuate guide rail and is movable along the arcuate guide rail. The loading system VIII is mounted to the rotary base VII. A steel ball of the loading system VIII and the glass disc are movable relative to each other. A rotary bearing in the rotary base is configured to convert a frictional force generated from the relative movement to a pressure allowed to be collected by a pressure sensor on the rotary base.

A rotary movement of a screw is converted to a linear motion of the translation stage IV along the guide rail by means of threaded driving, to realize contact between the steel ball and the glass disc, and a movement distance of the translation stage IV along the linear guide rail is adjusted to realize back and forth movement of a contact point between the ball and the disc, so as to make full use of the different guide rails of the glass disc. A multi-angle movement between the glass disc and the steel ball is restrained by using an arcuate guide rail fixed to the worktable. Since the steel ball can rotate within a stroke of the arcuate guide rail, a direction of relative movement between the ball and disc can vary to any angle from 0 degrees to 180 degrees by means of forward and reverse rotation of a driving motor, so as to measure a lubricating oil film and a frictional force in different surface velocity directions. The frictional force between the steel ball and the glass disc is converted to a positive pressure between a rod and a sensor by using the rotary bearing in the rotary base, so as to measure a component of the frictional force by using the pressure sensor, and the component of the frictional force is corrected by using an equation derived from a geometric relationship, to obtain an actual frictional force. By means of the loading system (a lever mechanism), the steel ball realizes loading of a lower surface of the glass disc, so as to measure an oil film and a frictional force under different loads. A microscope is placed above the contact point between the steel ball and the glass disc, and the microscope is fixed to one side of the translation stage. A position of a lens of the microscope may be tuned up, down, left, or right by using a nut to position an oil film image. The image is captured by using a CCD to form an oil film interference image. Finally, a center of an oil film of each point and a minimum thickness of the oil film are calculated by using an equation according to shapes, positions, and an order of interference fringes by means of an industrial computer, so as to realize measurement of the elastic fluid lubricant.

Figure 3:
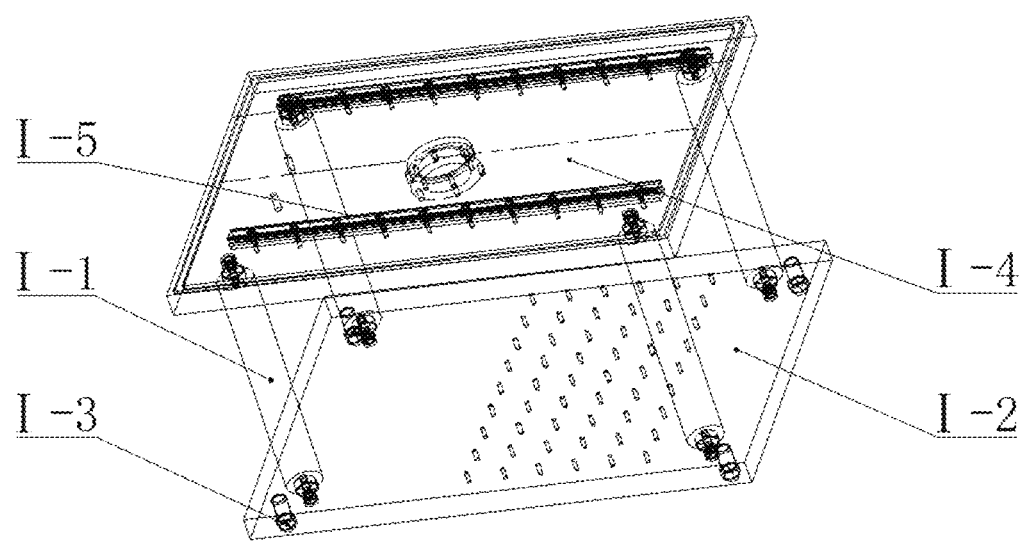
FIG. 3 is a schematic structural diagram of an experiment bench according to the present invention.

A specific structure of each part is as follows:

As shown in FIG. 3, the foregoing experiment bench I includes a support post I-1, a lower base plate I-2, support screws I-3, an upper table I-4, and linear guide rails I-5. The upper table I-4 and the lower base plate I-2 of the experiment bench each have provided thereon four threaded holes in an even distribution, and are connected by using four support posts I-1 each having threads on upper and lower ends. Four support screws I-3 are evenly mounted under the lower base plate I-2. By adjusting the four support screws I-3, a height of the entire experiment bench may be adjusted. Two parallel linear guide rails I-5 are disposed on a top of the upper table. Each linear guide rail I-5 has disposed thereon ten hexagon socket screws in an even distribution. The linear guide rails I-5 are connected and fixed to the upper table I-4 by using the hexagon socket screws to restrain the movement of the translation stage IV.

Figure 4:
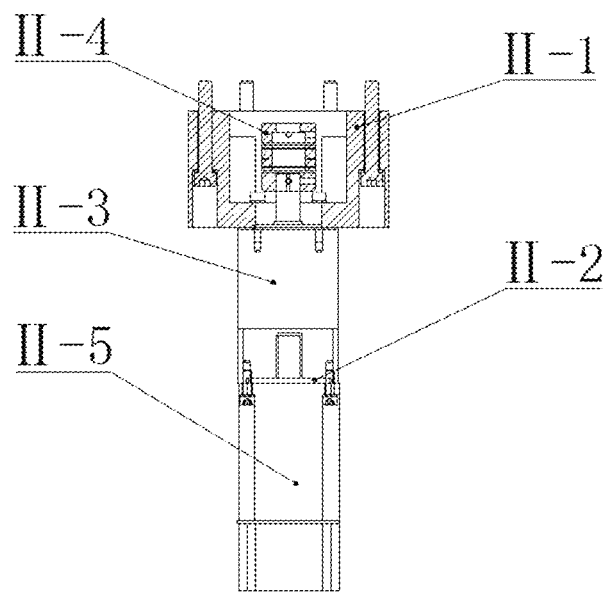
FIG. 4 is a schematic structural diagram of a main shaft driving system according to the present invention.

As shown in FIG. 4, the main shaft driving system includes a motor support post II-1, a motor vibration isolation pad II-2, a precise decelerator II-3, a threaded coupler II-4, and an HG-MR43 motor II-5. The motor vibration isolation pad II-2 is mounted to an end portion of an output shaft of the motor for vibration absorption and buffering during operation of the motor. The output shaft of the motor is connected to an input terminal of the precise decelerator II-3. An output terminal of the precise decelerator II-3 is connected to the threaded coupler II-4. A body of the precise decelerator II-3 is mounted to the motor support post II-1. The motor support post II-1 is mounted under the upper table I-4 by means of a screwed connection by using hexagon socket screws.

Figure 5:
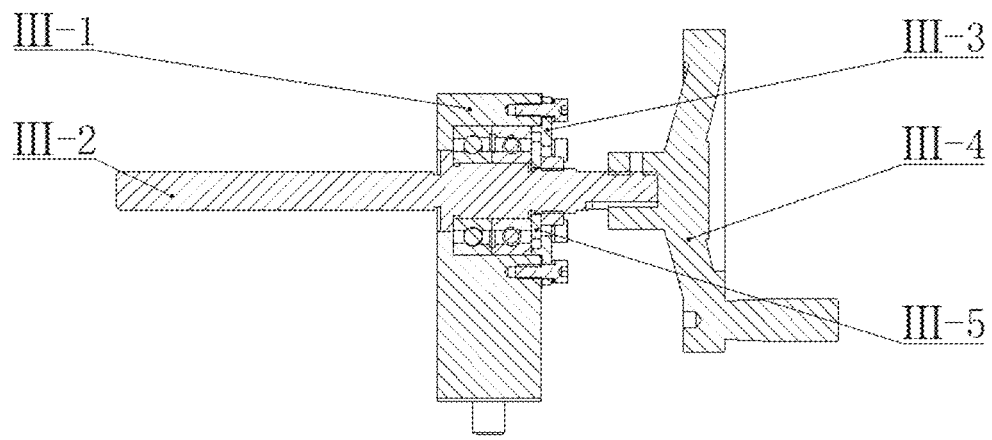
FIG. 5 is a schematic structural diagram of a translation stage driver according to the present invention.

As shown in FIG. 5, the translation stage driver includes a driving rear seat III-1, a translation driving rod III-2, a rear seat end cover III-3, a hand wheel III-4, and a retainer ring III-5. The driving rear seat III-1 is connected to a table of the translation stage by using screws, and a pair of angular contact ball bearings are mounted in the driving rear seat III-1. An outer bearing is compressed by using the rear seat end cover III-3 and the retainer ring III-5 mounted in the rear seat end cover III-3 to realize sealing. The translation driving rod III-2 extends through an inner ring of the bearing, the retainer ring III-5, and the rear seat end cover III-3 to be connected to the rear hand wheel III-4. The rear hand wheel III-4 is rotated clockwise and counterclockwise to control the translation stage to move forward and backward.

Figure 6:
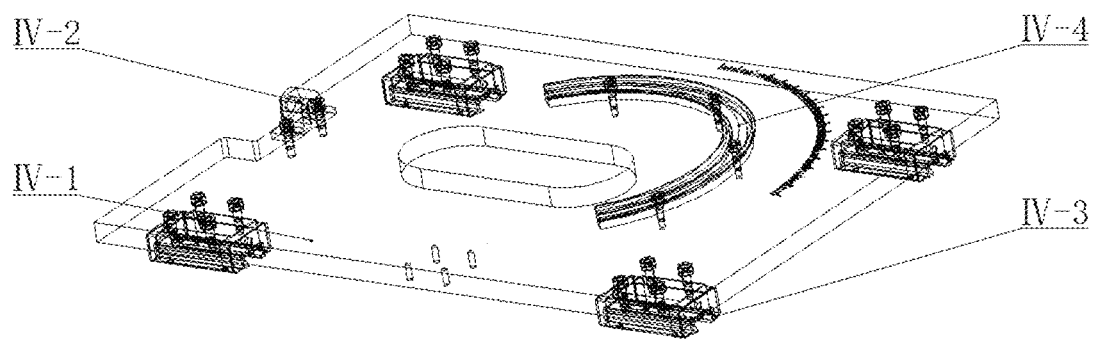
FIG. 6 is a schematic structural diagram of a translation stage according to the present invention.

As shown in FIG. 6, the translation stage includes a worktable IV-1, a threaded pitch adjusting seat IV-2, guide rail sliders IV-3, and an arcuate guide rail IV-4. Two pairs of guide rail sliders IV-3 are evenly distributed under the worktable IV-1. The guide rail sliders IV-3 are mated with the linear guide rail I-5 to realize the linear movement of the translation stage along the guide rail. The arcuate guide rail IV-4 is mounted above the worktable IV-1 to restrain the rotation of the rotary base so as to realize a variable angular movement of the ball and disc with a fixed contact point. The threaded pitch adjusting seat IV-2 is mounted to an other side above the worktable IV-1 and is threadedly connected to the translation driving rod III-2 to facilitate movement of the worktable IV-1.

Figure 7:
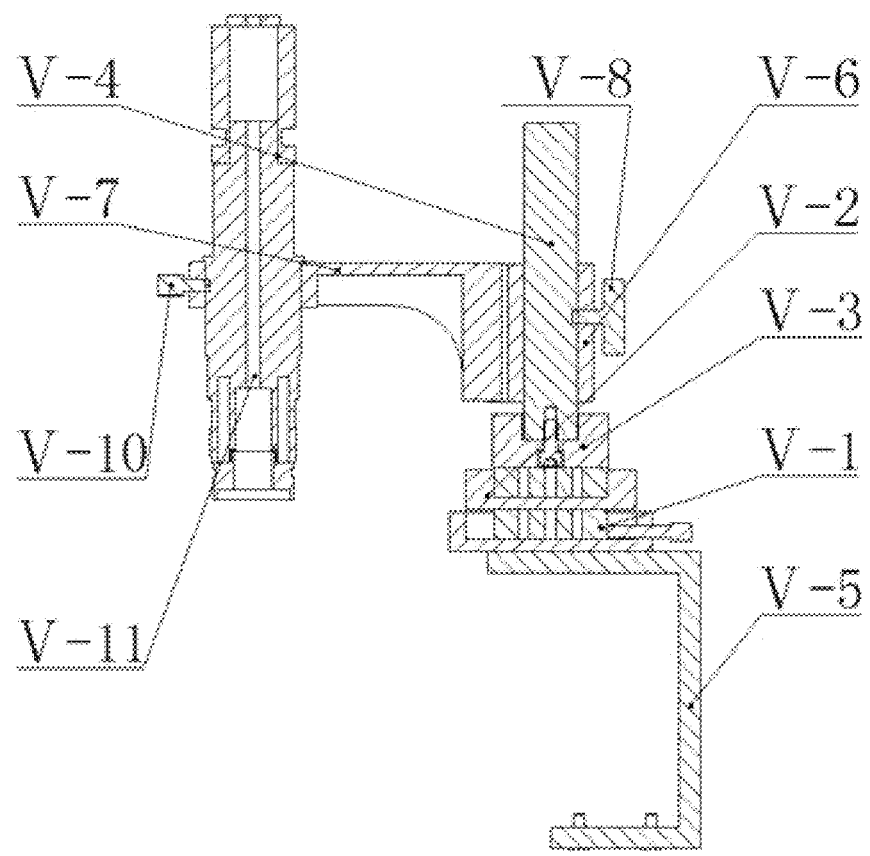
FIG. 7 is a schematic semi-cross-sectional view of an image capture system according to the present invention.
Figure 8:
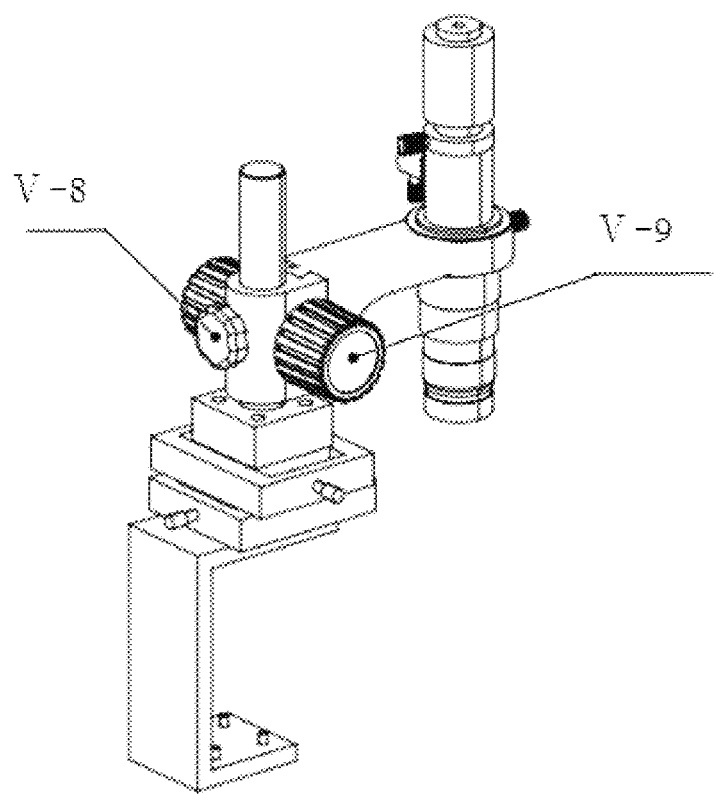
FIG. 8 is a schematic positive triaxial side view of the image capture system according to the present invention.

As shown in FIG. 7 and FIG. 8, the image capture system includes a first displacement stage V-1, a second displacement stage V-2, a connecting plate V-3, a support rod V-4, a microscope support V-5, a support rod bracket of microscope support V-6, a lens barrel bracket V-7, a hand wheel V-8, a focus wheel V-9, locking screws V-10, and a CCD and microscope V-11. A lower end of the microscope support V-5 is mounted to the worktable IV-1 by using screws, the first displacement stage V-1 and the second displacement stage V-2 are mounted to an upper end of the microscope support V-5, and the second displacement stage V-2 is located on the first displacement stage V-1. Peripheral positions of the two displacement stages may be tuned by adjusting nuts, so as to move a lens of the microscope to position an oil film interference image. A lower end of the connecting plate V-3 is threadedly connected to an upper end of the second displacement stage V-2, and an upper end of the connecting plate V-3 is fixedly connected to the support rod V-4. The support rod bracket of microscope support V-6 is sleeved on the support rod V-4 and is connected to the lens barrel bracket V-7. The hand wheel V-8 and the focus wheel V-9 are both mounted to the support rod bracket of microscope support V-6 to adjust a focus of the microscope and lift and lower the lens of the microscope, so as to adjust a definition of interference fringes in the oil film image. The locking screws V-10 are screwed into a front of the lens barrel bracket V-7 by using threads to fix a main body of the microscope, thereby avoiding movement of the image during observation. The CCD and microscope V-11 is mounted in the lens barrel bracket to realize image observation and data transmission.

Figure 9:
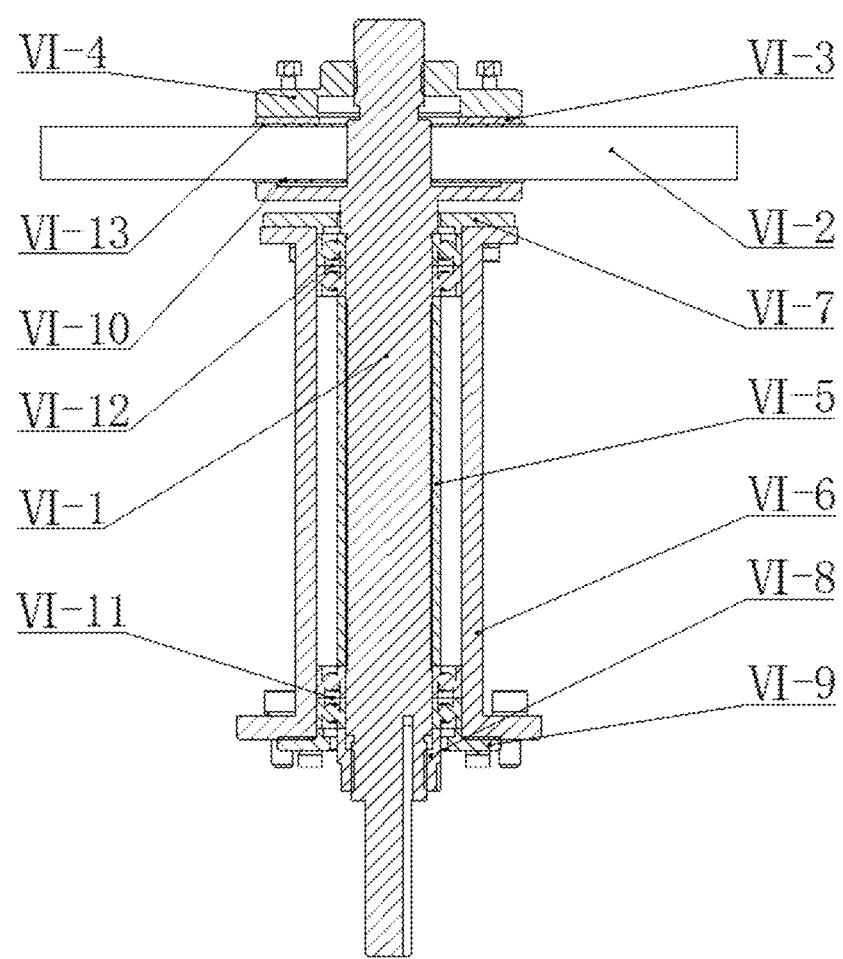
FIG. 9 is a schematic structural diagram of a main shaft system according to the present invention.

As shown in FIG. 9, the main shaft system includes a main shaft VI-1, a glass disc VI-2, a steel pad VI-3, a glass disc pressing sleeve VI-4, a shaft inner sleeve VI-5, an outer sleeve VI-6, an upper end cover VI-7, pre-tightening nuts VI-8, a lower end cover VI-9, a second rubber pad VI-10, a first bearing VI-11, a second bearing VI-12, and a first rubber pad VI-13.

The main shaft VI-1 is divided into an upper part and a lower part by using the glass disc VI-2 as a boundary. The upper end cover VI-7, the first bearing VI-11, the shaft inner sleeve VI-5, the second bearing VI-12, and the pre-tightening nuts VI-8 located at the lower part of the main shaft VI-1 are pressed and mounted in sequence. The first rubber pad VI-13, the glass disc VI-2, the second rubber pad VI-10, the steel pad VI-3, and the glass disc pressing sleeve VI-4 located at the upper part of the main shaft VI-1 are pressed and mounted in sequence. The outer sleeve VI-6 is sleeved on the lower part of the main shaft VI-1. A lower end of the outer sleeve VI-6 is threadedly connected to the upper table by using six hexagon socket screws. An upper end of the outer sleeve VI-6 is threadedly connected to the upper end cover VI-7 by using six hexagon socket screws. A lower end of the main shaft VI-1 is connected to the threaded coupler II-4. The main shaft VI-1 rotates under driving of the main shaft driving system to drive the glass disc VI-2 to rotate.

Figure 10:
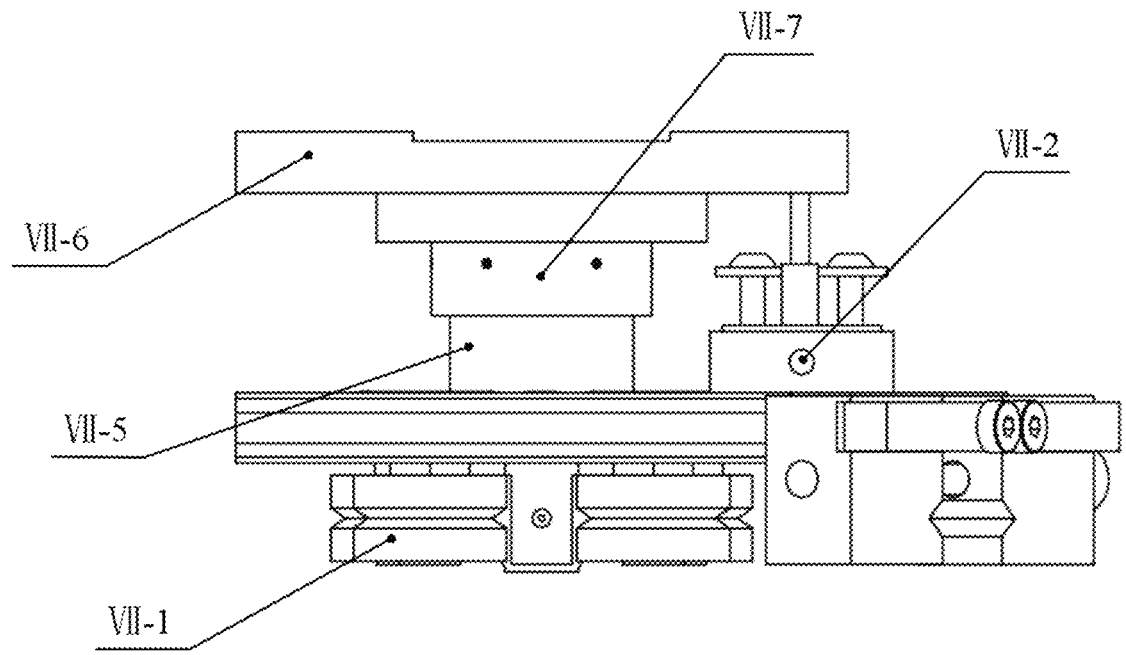
FIG. 10 is a front view of a rotary base structure according to the present invention.
Figure 11:
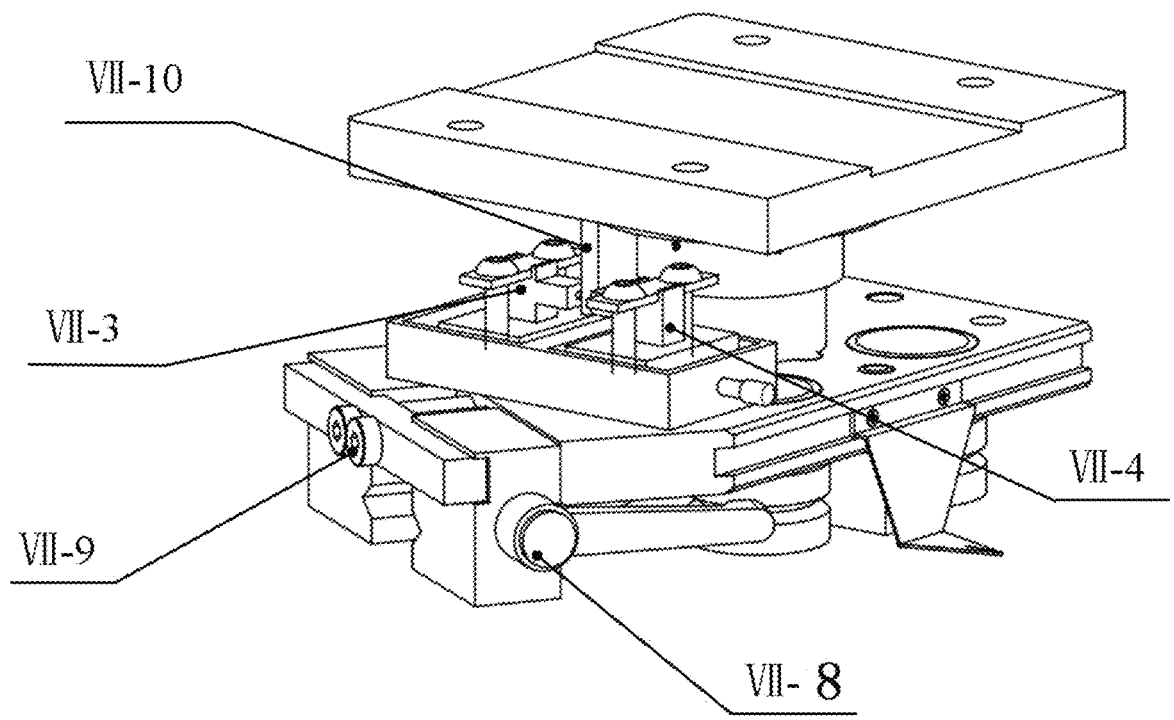
FIG. 11 is a schematic positive triaxial side view of the rotary base structure according to the present invention.
Figure 12:
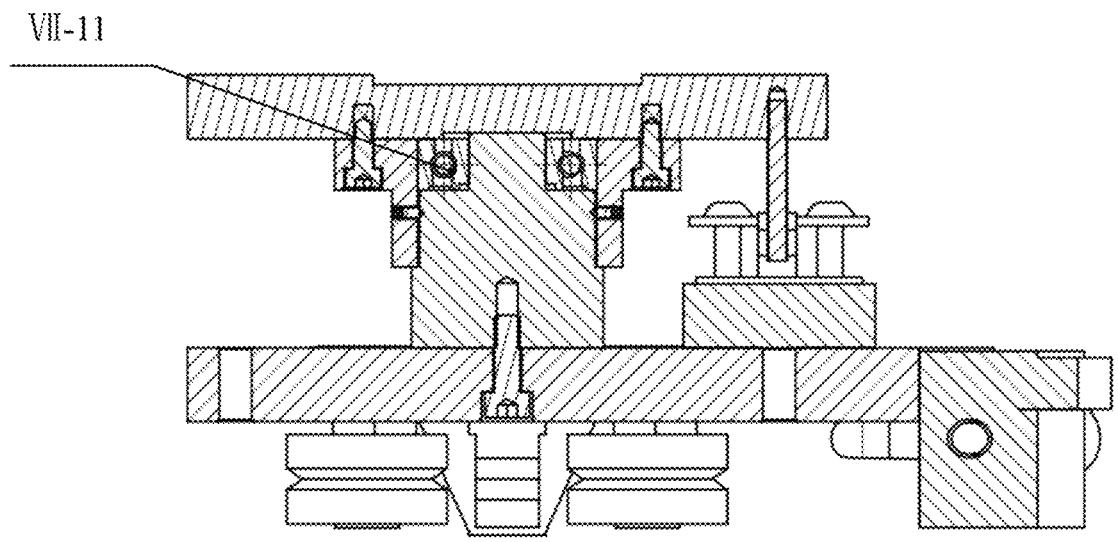
FIG. 12 is a front semi-cross-sectional view of the rotary base structure according to the present invention.

As shown in FIG. 10, FIG. 11, and FIG. 12, the rotary base includes a turnable positioning stage VII-1, a bidirectional translation stage VII-2, a first pressure sensor VII-3, a second pressure sensor VII-4, a turnable pillar VII-5, a loading base VII-6, a bearing seat VII-7, an adjustment handle VII-8, a fastening block VII-9, a rod VII-10, and a rotary bearing VII-11.

The turnable positioning stage VII-1 includes the fastening block VII-9 and the adjustment handle VII-8. The turnable positioning stage VII-1 is mounted to the arcuate guide rail IV-4 by using a roller and the fastening block. The first pressure sensor VII-3 and the second pressure sensor VII-4 are respectively mounted to two sides of the bidirectional translation stage VII-2 in opposite directions. The bidirectional translation stage VII-2 is mounted to one side of the turnable positioning stage VII-1 by using hexagon socket head screws. A center position of the bidirectional translation stage VII-2 is connected to a bottom of the loading base VII-6 by using the rod VII-10.

The turnable pillar VII-5 is in a three-step shape. A circular hole under the loading base VII-6 corresponds to a top of the turnable pillar VII-5. The turnable pillar VII-5 is inserted into the rotary bearing VII-11, and the rotary bearing VII-11 is mounted in the bearing seat VII-7. The bearing seat VII-7 is connected to the loading base VII-6 by using screws. The loading base VII-6, the bearing seat VII-7, and the turnable pillar VII-5 are mounted to the turnable positioning stage VII-1 in sequence from top to bottom.

Two sliders are mounted in the bidirectional translation stage VII-2. The first pressure sensor VII-3 is mounted to one of the sliders, and the second pressure sensor VII-4 is mounted to the other of the sliders. A bottom of each slider is threadedly mated with a threaded rod that is manually adjustable. By rotating the two threaded rods, face-to-face or opposite movement of the two pressure sensors can be realized.

Figure 13:
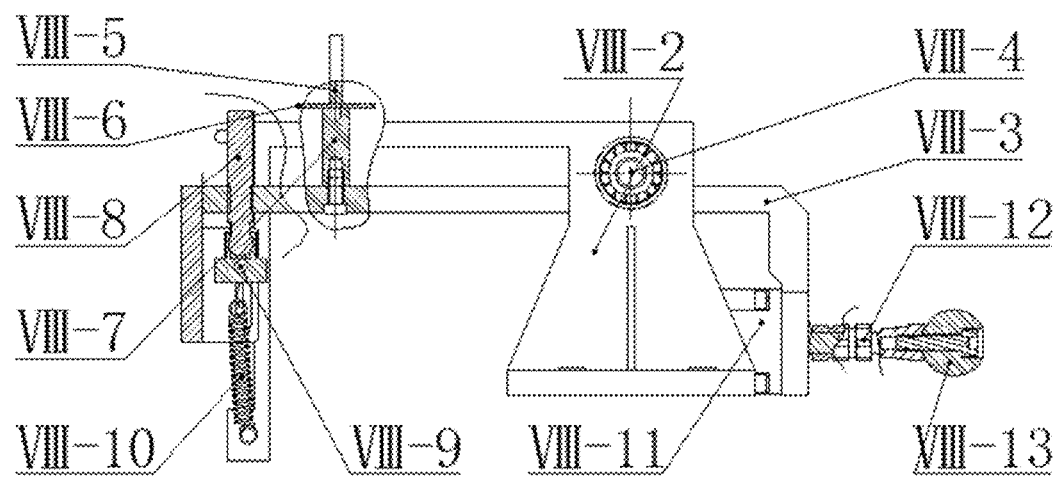
FIG. 13 is a left partial cross-sectional view of a loading system structure according to the present invention.
Figure 14:
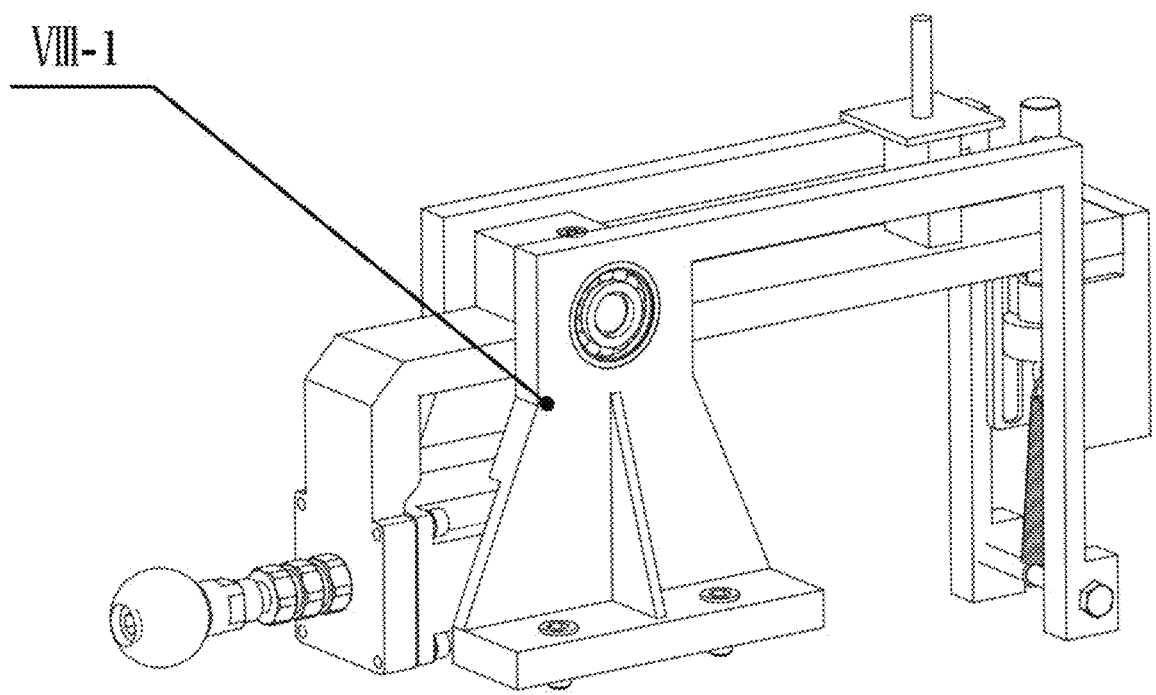
FIG. 14 is a schematic positive triaxial side view of the loading system structure according to the present invention.

As shown in FIG. 13 and FIG. 14, the loading system includes a first loading support VIII-1, a second loading support VIII-2, a loading lever VIII-3, fulcrum bearings a weight fixing rod VIII-5, a weight tray VIII-6, a weight support base VIII-7, a loading adjustment rod VIII-8, an adjustment guide block VIII-9, a spring VIII-10, a servo motor VIII-11, a rigid coupler VIII-12, and a steel ball VIII-13.

The first loading support VIII-1 and the second loading support VIII-2 are oppositely mounted to the loading base VII-6 by using screws. Two fulcrum bearings VIII-4 are respectively mounted in circular holes in the middle of the two supports. The loading lever VIII-3 extends through the fulcrum bearings VIII-4 to be mounted between the first loading support VIII-1 and the second loading support VIII-2 and is fastened by using screws, so that the loading lever VIII-3 can be rotated about a center and serve as a fulcrum to drive the steel ball to load the glass disc. The steel ball VIII-13 is composed of a ball rod and a steel ball body. A through hole exists in the middle of the steel ball, and the ball rod extends through a rear of the through hole and is fastened by using screws to be integrated with the steel ball. One end of the rigid coupler VIII-12 is connected to the steel ball VIII-13 by using threads of the rod, and an other end is connected to an output rod of the servo motor VIII-11 by using threads, thereby coupling the motor to the steel ball to realize power transfer. A main body of the servo motor VIII-11 is connected to a front end (the front end herein corresponds to a right end in FIG. 13) of the loading lever VIII-3 by using threads. The weight fixing rod VIII-5, the weight tray VIII-6, and the weight support base VIII-7 are mounted to a rear end (the rear end herein corresponds to a left end in FIG. 13) of the loading lever VIII-3 from top to bottom in sequence. The loading adjustment rod VIII-8 is connected to a rear end (the rear end herein corresponds to the left end in FIG. 13) of the loading lever VIII-3 by using threads, and the adjustment guide block VIII-9 and the spring VIII-10 are mounted to a lower end of the loading adjustment rod VIII-8 in sequence. The supports on two sides of the adjustment guide block VIII-9 have therein grooves matching the adjustment guide block. A circular ring at a lower end of the spring VIII-10 is sleeved on a bolt fixed in the middle of tails of the first loading support VIII-1 and the second loading support VIII-2, so as to be connected to the supports.

A test method corresponding to the foregoing device for measuring a frictional force and a film thickness of a lubricating oil film in different surface velocity directions is as follows.

During measurement of an oil film and a frictional force by using the experiment bench, the hand wheel is first driven by the translation stage driver to rotate, so as to move the translation stage IV away from the glass disc, a relatively small initial velocity is set for the glass disc by using a computer, so that the glass disc is slowly rotated, and the glass disc is cleaned by using special wipes. Then a clear guide rail with no scratches is selected from the glass disc. Upon oiling of the guide rail, the glass disc is stopped, so as to complete preparation of the glass disc.

Upon completion of the preparation of the glass disc, preparation for loading of the steel ball is then performed. A specific working process of a loading device is as follows: before loading of the steel ball, the steel ball is not allowed to be under the glass disc and needs to be at a certain distance from the glass disc, to prevent the steel ball from shaking suddenly and damaging the glass disc as a result of an unstable force during the preparation of the loading.

Upon start of the loading, the loading adjustment rod is adjusted so that the spring slowly receives a force under guidance of the adjustment guide block, and then the loading lever is slowly raised under support of the first loading support and the second loading support. When the steel ball is still 5-10 millimeter away from the glass disc, the hand wheel driven by the translation stage is rotated in a reverse direction to move the steel ball toward the glass disc and ensure that a contact point between the ball and the disc is located on the oiled guide rail of the glass disc, thereby completing positioning of the contact point between the ball and the disc. Then the loading adjustment rod is rotated again to realize spontaneous contact between the steel ball and the glass disc. At this time, the preparation for the loading is completed, but the loading is not performed.

Upon completion of the preparation for the loading, an angle of motion of the steel ball is adjusted by using the rotary base. A working process of the rotary base is as follows: during the adjustment of the angle of the steel ball, a fastening handle of the turnable positioning stage is first loosened to loosen the fastening block therein, so that the turnable positioning stage is no longer fastened and is movable along the arcuate guide rail, then the loading system on the rotary base is rotated until the stroke angle scale reaches a predetermined angle, and the adjustment handle is adjusted in a reverse direction so that the fastening block is moved inward perpendicular to the arcuate guide rail, to fix the turnable positioning stage, which also ensures a fixed direction of an entrainment velocity, thereby completing the adjustment of the angle of motion of the steel ball.

Upon completion of the adjustment of the angle of the steel ball, the steel ball may be loaded. Only a fixed weight needs to be added to the weight fixing rod. The added weight may change a force direction by using an equal-arm loading lever to load the steel ball. A magnitude of a loading force is a gravity of the weight obtained by mans of equivalent conversion. So far, the loading is completed.

Upon completion of the loading work, the oil film may be observed. A specific implementation of the measurement of the oil film of the present invention is as follows: the first displacement stage and the second displacement stage in the image capture system are first adjusted to move a point contact image of the ball and the disc after the loading to a center of a field of view of the microscope, and then the hand wheel and the focus wheel are adjusted to complete focusing, so as to obtain an oil film interference pattern having clear interference fringes. Upon completion of the focusing, two motors are controlled by using computer software to provide corresponding velocities to the steel ball and the glass disc for rotation. Upon start of rotation of the disc, the first displacement stage and the second displacement stage are adjusted again to compensate for deviation of the oil film interference image due to the rotation of the ball disc. The oil film interference image may be captured by the CCD and camera software and transmitted to a computer to be saved as a picture.

In addition to the functions of observing and capturing the oil film interference image, the present invention further provides a function of measuring a frictional force of a point contact oil film in different surface velocity directions. A specific implementation is as follows. A positive direction needs to be specified first. In this embodiment, it is assumed that clockwise rotation of the steel ball viewed from the servo motor connected to the steel ball is forward rotation, and counterclockwise rotation of the steel ball viewed from here is reverse rotation. Since an experimental condition of this embodiment is different velocity directions, which means that a direction of the entrainment velocity varies during the experiment and that a direction of the frictional force also varies, the measurement of the frictional force includes two situations according to angles. Details are as follows.

A first step is to measure a frictional force between the steel ball and the glass disc on the oil film when the stroke angle scale is between 0 degrees and 90 degrees. An experimenter first needs to move the turnable positioning stage so that a stroke angle measure of the turnable positioning stage is at 0 degrees, and then the bidirectional translation stage is adjusted so that the pressure sensor on a side close to the steel ball is far away from a stud and the pressure sensor on a side away from the steel ball is close to the stud. At this time, the servo motor is turned on to rotate in a forward direction. Parts above the bearing seat receive a frictional force in a counterclockwise direction of the loading base, and the pressure sensor away from the steel ball receives a pressure. The pressure is a component of the frictional force that needs to be measured in this embodiment. In this way, the measurement of the component of the frictional force component that is perpendicular to a direction of the rod of the steel ball in case of an acute velocity angle is completed.

A second step is to measure a frictional force between the steel ball and the glass disc on the oil film when the stroke angle measure is between 90 degrees and 180 degrees. An experimenter first adjusts an adjustment knob of the bidirectional translation stage, so that the pressure sensor on a side away from the steel ball is away from the stud and the pressure sensor on a side close to the steel ball is close to the stud. At this time, the servo motor is turned on to rotate in a reverse direction. Other experimental work is similar to the steps of measuring the frictional force between the steel ball and the glass disc between 0 degrees and 90 degrees. Finally, an indicator of the component of the frictional force is read from the pressure sensor on an other side, to complete the measurement of the component of the frictional force that is perpendicular to the direction of the rod of the steel ball in case of an obtuse velocity angle. The component is then corrected to obtain a total frictional force. So far, complete relationships between frictional forces within 0 degrees to 180 degrees and different angles of motion of the steel ball and glass disc and complete measurement steps can be obtained.

During the measurement of the point contact oil film with a varied angle, the oil film is sandwiched between the steel ball and the glass disc to form a sandwich-like model. The frictional force to be measured in this embodiment is a frictional force on the oil film. A total frictional force includes a frictional force between the disc and the oil film and a frictional force between the steel ball and the oil film. Directions of the two frictional forces are respectively opposite to directions of a velocity of the ball a velocity of the disc. Since direction of the velocity of the ball and the direction of the velocity of the disc during the experiment cannot always be the same, that is, the surface velocity directions are different, a direction of an actual total frictional force is not in a straight line with the direction of the velocity of the ball, instead, an angle exists therebetween. Therefore, the pressure measured by the force sensor in this embodiment is not the actual frictional force on the oil film, but a component of the frictional force in an axial direction perpendicular to the direction of the rod of the steel ball. In order to obtain the actual resultant frictional force, the measured component in this embodiment needs to be corrected. According to literatures, a direction of a frictional force has nothing to do with a motion direction of an object. Instead, the direction of a frictional force is opposite to a direction of relative motion or a direction of a relative motion trend. The frictional force to be measured in this embodiment is actually a shear force generated by the oil on the ball and oil in different layers of the disc in different motion directions. Therefore, in order to obtain the frictional force, a relative motion direction between the oil on the ball and the oil on the disc is required, which is actually a relative velocity direction between the steel ball and the glass disc. Therefore, correcting the frictional force actually means obtaining the relative motion velocity direction by using the geometric relationship between the velocity of the ball and the velocity of the disc. In fact, the direction is the direction of the frictional force. Then, according to a vector calculation and the geometric relationship, the actual frictional force on the oil film is obtained by using the measured frictional force component in this embodiment as a known factor. The above is theoretical explanation for the correction for the frictional force measurement.

It needs to be first noted that, a simplified diagram of a model for measuring a frictional force of a point contact with a varied angle is drawn to analyze forces on a frictional force model under various angles to obtain an expression of the frictional force. $u_b$ is the velocity of the ball, $u_d$ is the velocity of the disc, $\alpha$ is an angle by which the disc is deflected, and $F_1$ is the force measured by the sensor. $f_d$ is the frictional force between the oil film and the glass disc, and $f_b$ is the frictional force between the oil film and the steel ball. Due to different deflection angles between the velocity of the ball and the velocity of the disc, directions of the frictional forces constantly vary. Therefore, the correction of the frictional force includes four situations.

In a first situation, the angle between the velocities is 0 degrees, that is, the velocity of the ball and the velocity of the disc are the same. Analysis of a motion model and a force in this working situation are usually as follows.

It is easily learned from the figure that the actual frictional force is indeed perpendicular to the direction of the rod of the steel ball, and has only one direction, that is, a direction always opposite to the directions of the velocity of the ball and the velocity of the disc. Therefore, a pressure indicator obtained from the sensor in this embodiment is actually the total frictional force on the oil film.

In a second situation, a deflection angle between the velocity of the ball and the velocity of the disc is an acute angle. In this case, the velocity of the ball and the velocity of the disc are not in a straight line. A relative velocity between the velocity of the ball and the velocity of the disc is required to be solved according to a geometric relationship.

It should be noted that, specific ideas for correcting the frictional force under such an angle are as follows. First of all, the velocity of the ball and the velocity of the disc are known as $u_b$ and $u_d$. Actually, $u_b$ and $u_d$ are respectively a velocity of the ball relative to the ground and a velocity of the disc relative to the ground. According to a relative motion equation of $u_{b\ versus\ d} = u_{b\ versus\ ground} + u_{ground\ versus\ b}$, by means of negation of $u_b$, $u_{b\ versus\ d} = u_{b\ versus\ ground} - u_{d\ versus\ ground}$ is obtained. Therefore, $u_{bd} = u_b - u_d$, which is the relative velocity of the ball and the disc. Then, according to the vector subtraction, a difference between the velocity of the ball and the velocity of the disc is acquired to obtain a relative velocity direction, that is, an actual total frictional direction. At this time, the direction of the total frictional force is known. In addition, in this embodiment, the frictional force is divided into a force perpendicular to the direction of the rod of the steel ball and a force in the direction of the rod of the steel ball. The force perpendicular to the direction of the steel rod of the steel ball is the force measured by the pressure sensor. If the direction of the other force is known, the magnitude and the direction of the actual frictional force can be drawn by using a vector triangle. Then the unknown angle is converted to a geometric relationship between the known velocities by using auxiliary line according to the known angle relationship, to obtain an equation for correcting the frictional force.

Figure 15:
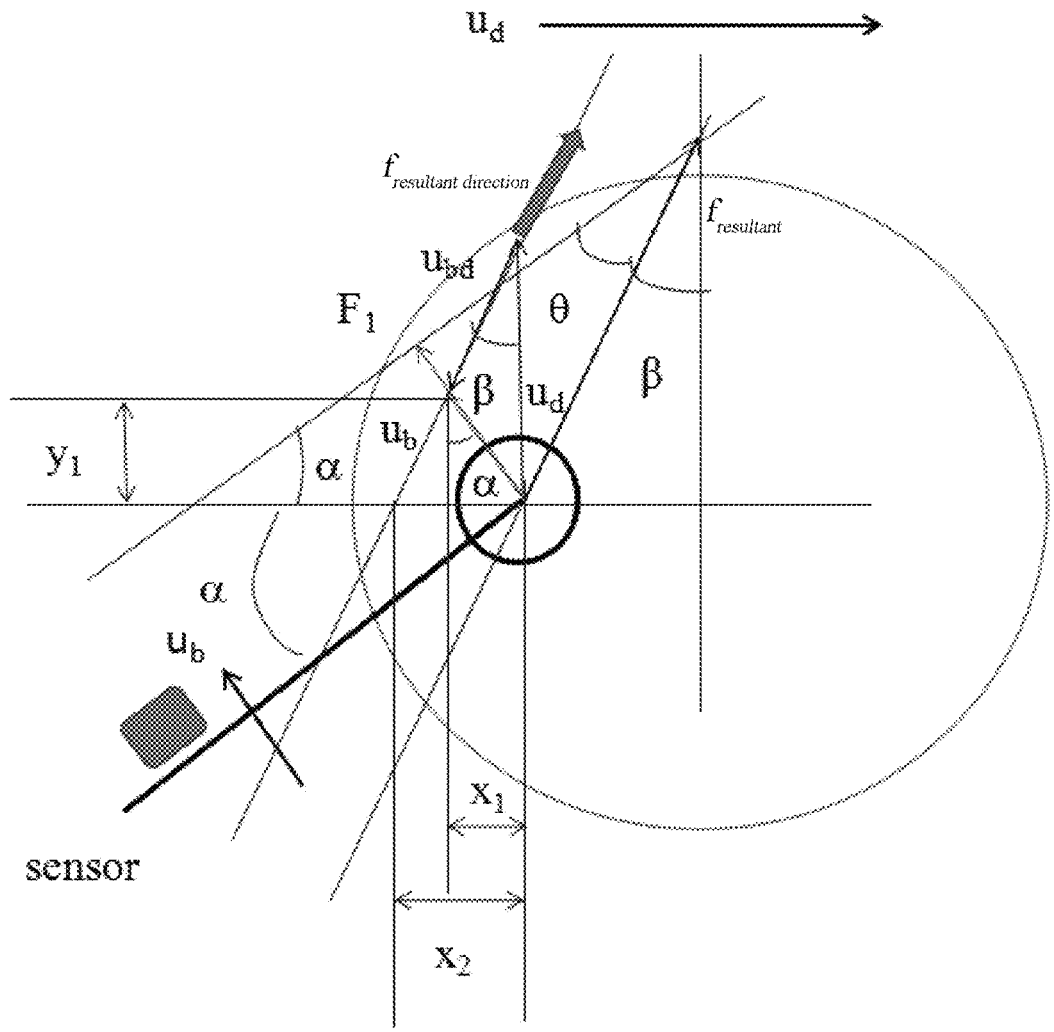
FIG. 15 is a schematic diagram of analysis of a specific motion model and a force when a deflection angle between a ball and a disc is an acute angle.

FIG. 15 shows analysis of a specific motion model and a force when the deflection angle between the ball and the disc is an acute angle. Details of the analysis are as follows.

Measurement equations for the frictional force and a derivation process are as follows:

$$x_1 = u_b \cdot \sin\alpha;$$

$$x_2 = u_d \cdot \tan\beta;$$

$$y_1 = u_b \cdot \cos\alpha;$$

$$\tan\beta = \frac{x_2 - x_1}{y_1} = \frac{u_d \cdot \tan\beta - u_b \cdot \sin\alpha}{u_b \cdot \cos\alpha};$$

$$\tan\beta = \frac{-u_b \cdot \sin\alpha}{u_b \cdot \cos\alpha - u_d};$$

$$\beta = \arctan-\frac{u_b \cdot \sin\alpha}{u_b \cdot \cos\alpha - u_d};$$

$$\theta = \frac{\pi}{2} - \alpha - \beta = \frac{\pi}{2} - \alpha - \arctan\frac{-u_b \cdot \sin\alpha}{u_b \cdot \cos\alpha - u_d};$$

$$f_{resultant} = \frac{F_1}{\sin\theta} = \frac{F_1}{\sin\left(\frac{\pi}{2} - \alpha - \arctan\frac{-u_b \cdot \sin\alpha}{u_b \cdot \cos\alpha - u_d}\right)}.$$

According to the geometric relationship between the velocities and the auxiliary lines that are made, the direction of the actual frictional force on the oil film when the angle between the velocity of the ball and the velocity of the disc is an acute angle can be obtained, as shown in FIG. 15. The magnitude of the frictional force is shown in the foregoing equations. Since each variable is known and measurable, $f_{resultant}$ may be obtained.

In a third situation, the deflection angle between the velocity of the ball and the velocity of the disc is an obtuse angle. In this working situation, the frictional force of the oil film, the velocity direction of the glass disc, and the velocity direction of the steel ball are not in the same straight line. A relative velocity between the frictional force and the velocity of the disc is obtained according to the geometric relationship. A specific thinking process is similar to that when the angle is an acute angle.

Figure 16:
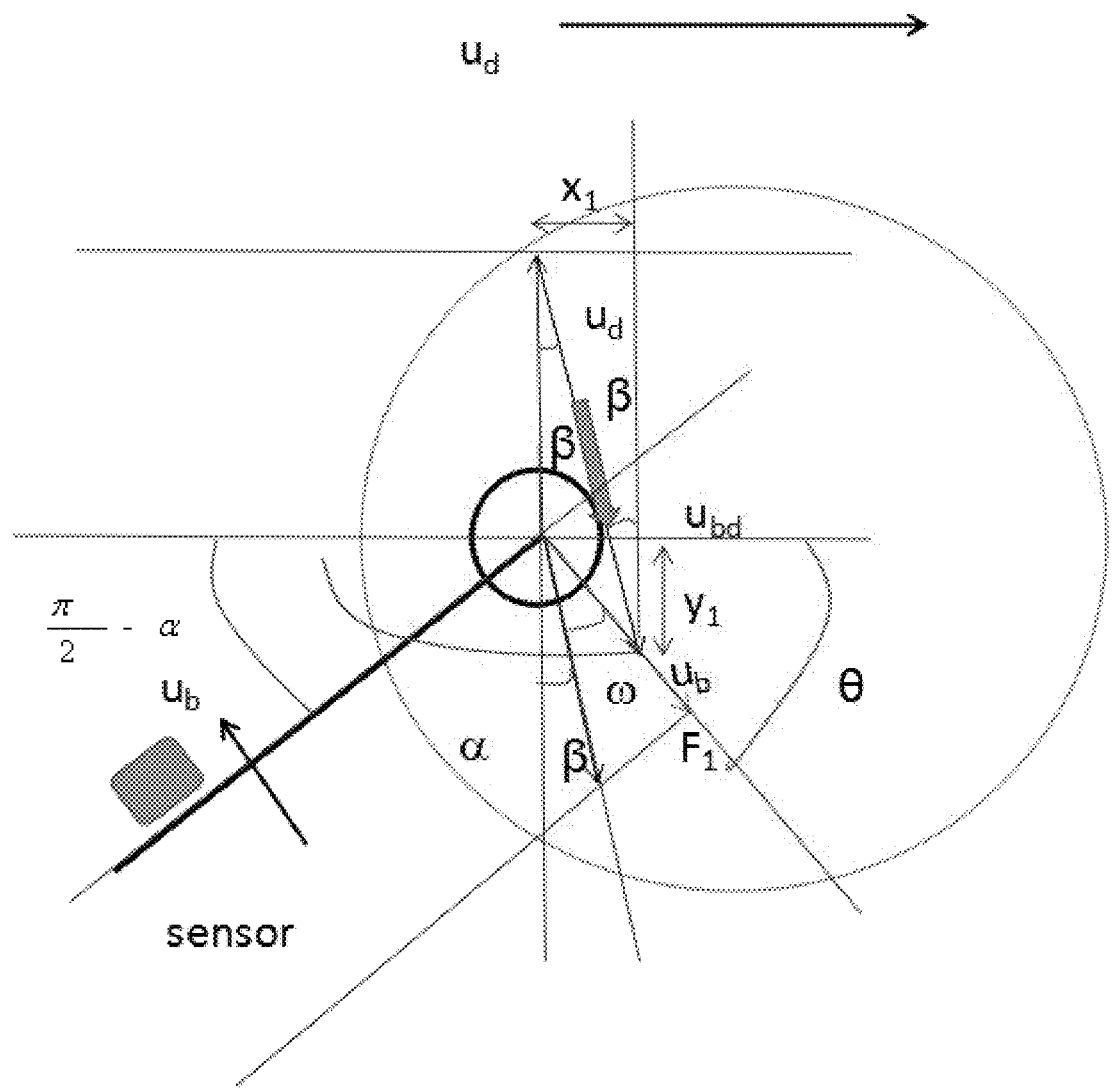
FIG. 16 is a schematic diagram of analysis of a motion model and a force when the deflection angle between the ball and the disc is an obtuse angle.

FIG. 16 shows analysis of a specific motion model and a force when the deflection angle between the ball and the disc is an obtuse angle. A specific process is follows.

$$\theta = \pi - \alpha;$$

$$y_1 = u_b \cdot \sin\theta = u_b \cdot \sin(\pi - \alpha) = u_b \cdot \sin\alpha;$$

$$\omega = \alpha - \frac{\pi}{2} - \beta = \alpha - \frac{\pi}{2} - \arctan\frac{-u_b \cdot \cos\alpha}{u_d + u_b \cdot \sin\alpha};$$

$$x_1 = u_b \cdot \cos\theta = u_b \cdot \cos(\pi - \alpha) = -u_b \cdot \cos\alpha;$$

$$\tan\beta = \frac{x_1}{u_d + y_1} = \frac{-u_b \cdot \cos\alpha}{u_d + u_b \cdot \sin\alpha};$$

$$\beta = \arctan\frac{-u_b \cdot \cos\alpha}{u_d + u_b \cdot \sin\alpha};$$

$$f_{resultant} = \frac{F_1}{\cos\omega} = \frac{F_1}{\cos\left(\alpha - \frac{\pi}{2} - \arctan\frac{-u_b \cdot \cos\alpha}{u_d + u_b \cdot \sin\alpha}\right)}.$$

According to the geometric relationship between the velocities and the auxiliary lines, the direction of the actual frictional force on the oil film when the angle between the velocity of the ball and the velocity of the disc is an obtuse angle may be obtained, as shown in FIG. 16. The magnitude of the frictional force is shown in the foregoing equations. Since each variable is known and measurable, $f_{resultant}$ may be obtained.

In a fourth situation, the deflection angle between the velocity of the ball and the velocity of the disc is a straight angle. In this working situation, the directions of the velocity of the ball and the velocity of the disc are opposite, and therefore the relative motion velocity is a vector difference between the velocity of the ball and the velocity of the disc. After the acquisition of the difference between the velocity of the ball and the velocity of the disc, the velocity of the ball is still perpendicular to the rod of the steel ball. Therefore, the actual frictional direction is still perpendicular to the direction of the rod of the steel ball. However, the specific direction herein depends on the velocity of the ball and the velocity of the disc, which includes two situations of a front direction and a rear direction. This corresponds to the two force sensors disposed in the experiment bench of the embodiments, so that front and back forces may be measured. In this case, the pressure on the sensor is the actual total frictional force on the oil film.

What is claimed is:

1. A device for measuring a frictional force and a film thickness of a lubricating oil film in different surface velocity directions, the device comprising a translation stage and a main shaft, wherein the translation stage is linearly movable under driving of a first driving device, the main shaft extends through the translation stage, a glass disc is fixed to an upper part of the main shaft, a lower part of the main shaft is driven by a second driving device to rotate, an arcuate guide rail is disposed on the translation stage, a rotary base is mounted to the arcuate guide rail and is movable along the arcuate guide rail, a loading system is mounted to the rotary base, a steel ball of the loading system and the glass disc are movable relative to each other, and a rotary bearing in the rotary base is configured to convert a frictional force generated from the relative movement to a pressure allowed to be collected by a pressure sensor on the rotary base.

2. The device for measuring a frictional force and a film thickness of a lubricating oil film in different surface velocity directions according to claim 1, wherein the rotary base comprises a turnable positioning stage, a loading base, a turnable shaft, and a bidirectional translation stage, the turnable positioning stage is mounted to the arcuate guide rail by using rollers, a top is connected to the loading base by using the turnable shaft and the rotary bearing, the bidirectional translation stage is mounted to one side of the turnable positioning stage, the bidirectional translation stage is connected to the loading base by using a rod, and two pressure sensors are mounted to two sides of the bidirectional translation stage, the two pressure sensors comprising a first pressure sensor and a second pressure sensor.

3. The device for measuring a frictional force and a film thickness of a lubricating oil film in different surface velocity directions according to claim 2, wherein the bidirectional translation stage comprises a body, two sliders are mounted in the body, the first pressure sensor is mounted to one of the sliders, the second pressure sensor is mounted to the other of the sliders, and a bottom of each slider is threadedly mated with a threaded rod that is manually adjustable.

4. The device for measuring a frictional force and a film thickness of a lubricating oil film in different surface velocity directions according to claim 2, wherein four circular truncated cone rollers are mounted to a bottom of the turnable positioning stage, grooves of the rollers are mated with an upper edge of the arcuate guide rail, the rollers are slidable along the guide rail, and the four rollers are evenly distributed on left and right sides of the guide rail to form a V-shaped constraint fitting the arcuate guide rail.

5. The device for measuring a frictional force and a film thickness of a lubricating oil film in different surface velocity directions according to claim 1, wherein the loading system comprises a loading support, a loading lever, fulcrum bearings, a loading adjustment rod, and the steel ball, the loading support is mounted to the rotary base, the two fulcrum bearings are respectively mounted in circular holes in the middle of the loading support, the loading lever extends through the fulcrum bearings to be mounted in the middle of the loading support, one end of the loading lever is connected to a servo motor, the servo motor is connected to the steel ball by using a rigid coupler, and a loading weight and the loading adjustment rod are mounted to an other end of the loading lever.

6. The device for measuring a frictional force and a film thickness of a lubricating oil film in different surface velocity directions according to claim 5, wherein the loading adjustment rod is threadedly connected to a rear end of the loading lever, an adjustment guide block and a spring are mounted to a lower end of the loading adjustment rod in sequence, and a lower end of the spring is connected to the loading support by using a connector.

7. The device for measuring a frictional force and a film thickness of a lubricating oil film in different surface velocity directions according to claim 5, wherein a weight support base is mounted to a rear end of the loading lever, a weight fixing rod is mounted to the weight support base, and a weight tray is mounted to the weight fixing rod.

8. The device for measuring a frictional force and a film thickness of a lubricating oil film in different surface velocity directions according to claim 5, wherein one end of the rigid coupler is connected to the steel ball by using threads of a rod, an other end is connected to an output rod of the servo motor by using threads, and a main body of the servo motor is connected to a front end of the loading lever by using threads.

9. The device for measuring a frictional force and a film thickness of a lubricating oil film in different surface velocity directions according to claim 1, the device further comprising an image capture system, wherein the image capture system comprises a displacement stage, a microscope support, a lens barrel bracket, a hand wheel, a focus wheel, a CCD, and a microscope, the displacement stage is mounted to a top of the microscope support, a support rod is mounted to the displacement stage, a support rod bracket of the microscope support is sleeved on the support rod and connected to the lens barrel bracket, the hand wheel and the focus wheel are mounted to the support rod bracket of the microscope support, and the CCD and the microscope are mounted in the lens barrel bracket to realize image observation and data transmission.

10. The device for measuring a frictional force and a film thickness of a lubricating oil film in different surface velocity directions according to claim 1, wherein the first driving device is a screw rod and nut pair driving device, and the second driving device is a motor driving device.

* * * * *